United States Patent
Ochiya

(10) Patent No.: US 10,337,012 B2
(45) Date of Patent: Jul. 2, 2019

(54) METHOD AND COMPOSITION FOR THE TREATMENT, PREVENTION, AND DIAGNOSIS OF CANCER CONTAINING OR DERIVED FROM CANCER STEM CELLS

(71) Applicants: 3-D MATRIX, LTD., Tokyo (JP); NATIONAL CANCER CENTER, Tokyo (JP)

(72) Inventor: Takahiro Ochiya, Tokyo (JP)

(73) Assignees: 3-D Matrix, Ltd., Tokyo (JP); National Cancer Center, Tokyo (JP)

( * ) Notice: Subject to any disclaimer, the term of this patent is extended or adjusted under 35 U.S.C. 154(b) by 0 days.

(21) Appl. No.: 15/410,480

(22) Filed: Jan. 19, 2017

(65) Prior Publication Data
US 2017/0240902 A1 Aug. 24, 2017

Related U.S. Application Data

(62) Division of application No. 13/817,763, filed as application No. PCT/JP2011/064527 on Jun. 24, 2011, now abandoned.

(30) Foreign Application Priority Data

Aug. 20, 2010 (JP) ................................. 2010-184764

(51) Int. Cl.
| | | |
|---|---|---|
| C12N 15/113 | (2010.01) | |
| G01N 33/574 | (2006.01) | |
| C12Q 1/6886 | (2018.01) | |
| A61K 31/7105 | (2006.01) | |

(52) U.S. Cl.
CPC ...... *C12N 15/1137* (2013.01); *A61K 31/7105* (2013.01); *C12Q 1/6886* (2013.01); *C12Y 204/99018* (2015.07); *G01N 33/574* (2013.01); *G01N 33/57415* (2013.01); *C12N 2310/14* (2013.01); *C12N 2310/3513* (2013.01); *C12N 2310/531* (2013.01); *C12N 2320/32* (2013.01); *C12Q 2600/106* (2013.01); *C12Q 2600/118* (2013.01); *C12Q 2600/158* (2013.01); *G01N 2333/91097* (2013.01)

(58) Field of Classification Search
CPC .............. C12N 15/113; C12N 2310/14; A01K 2207/05
See application file for complete search history.

(56) References Cited

U.S. PATENT DOCUMENTS

| | | |
|---|---|---|
| 8,106,024 B2 | 1/2012 | Ochiya et al. |
| 9,133,484 B2 | 9/2015 | Yoshida et al. |
| 2010/0087507 A1 | 4/2010 | Ochiya et al. |
| 2010/0186103 A1 | 7/2010 | Gao et al. |
| 2011/0152203 A1 | 6/2011 | Yoshida et al. |
| 2012/0252881 A1* | 10/2012 | Ochiya .............. A61K 31/7088 514/44 R |
| 2013/0236891 A1 | 9/2013 | Ochiya |

FOREIGN PATENT DOCUMENTS

| | | |
|---|---|---|
| EP | 2 322 608 A1 | 5/2011 |
| WO | 2007/144985 A1 | 12/2007 |
| WO | 2009/009739 A2 | 1/2009 |
| WO | 2010/024262 A1 | 3/2010 |

OTHER PUBLICATIONS

Jordan et al. NEJM 2006 355:1253-1261.*
Allen et al., "Visualization and enrichment of live putative cancer stem cell populations following p53 inactivation or Bax deletion using non-toxic fluorescent dyes", Cancer Biology & Therapy, vol. 8, No. 22, 2009, pp. 101-112.
Cicalese et al., "The Tumor Suppressor p53 Regulates Polarity of Self-Renewing Divisions in Mammary Stem Cells", Cell, vol. 138, No. 6, 2009, pp. 1083-1095.
Clevers, "The cancer stem cell: premises, promises and challenges", Nature Medicine, (Mar. 2011), vol. 17, No. 3, pp. 313-319.
European Patent Office Search Report dated Jul. 16, 2014 for Application No. 11817992.8.
Gupta et al.,"Identification of Selective Inhibitors of Cancer Stem Cells by High-Throughput Screening", Cell, (Aug. 2009) vol. 138, No. 4, pp. 645-659.
Honma et al., "RPN2 gene confers docetaxel resistance in breast cancer", Nature Medicine, (Sep. 2008) vol. 14, No. 9, pp. 939-948.
Ochiya, "Novel mechanisims of drug resistance in cancer", Seikagaku, (2010), vol. 82(a), pp. 34-38, and partial English translation attached.
Ochiya, "Nyugan no Yakuzai Teikosei ya Ten'ino o Seigyo suru Shinki Bunshi no Kaimei", Saishin Igaku, (Jun. 25, 2010) vol. 65, pp. 1343-1352. A partial English Translation is attached.
PCT/ISA/210—International Search Report dated Sep. 6, 2011, issued in PCT/JP2011/064527.
PCT/ISA/237—Written Opinion of the International Searching Authority dated Sep. 6, 2011, issued in PCT/JP2011/064527.
Takahashi et al., "RPN2 exerts a functional role in supporting cancer stem cell phenotype", Proceedings of the Japanese Cancer Association, vol. 68, 2009, p. 69.
Takahashi et al., "Cancer Stem Cells in Breast Cancer", Cancers, (2011) vol. 3, No. 1, pp. 1311-1328.
Takahashi et al., "Ribophorin II regulates breast tumor initiation and metastasis through the functional suppression of GSK3B", Scientific Reports, (Aug. 2013), vol. 3, pp. 1-13.
Tominaga et al., "RPN2-mediated glycosylation of tetraspanin CD63 regulates breast cancer cell malignancy", Molecular Cancer, (2014) vol. 13, p. 134 (1-11).
Von Maltzahn et al. Langmuir 2003, 19, 4332-4337.

* cited by examiner

*Primary Examiner* — Brian Whiteman
(74) *Attorney, Agent, or Firm* — IP Supra, PLLC; Constantine Linnik

(57) ABSTRACT

The invention provides a method and composition for the treatment, prevention, and diagnosis of cancer containing or derived from cancer stem cells.

12 Claims, 8 Drawing Sheets
Specification includes a Sequence Listing.

FIG. 1A
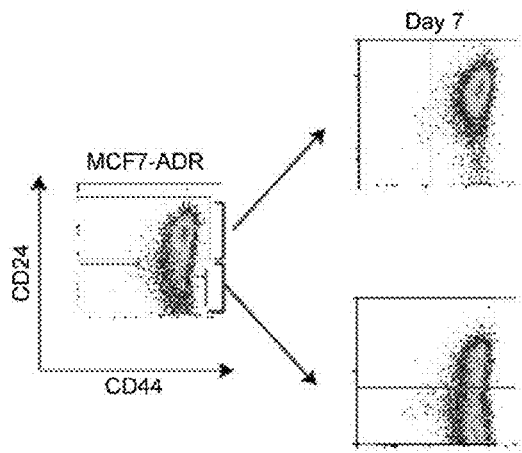
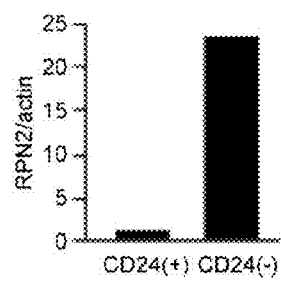
FIG. 1B
FIG. 2
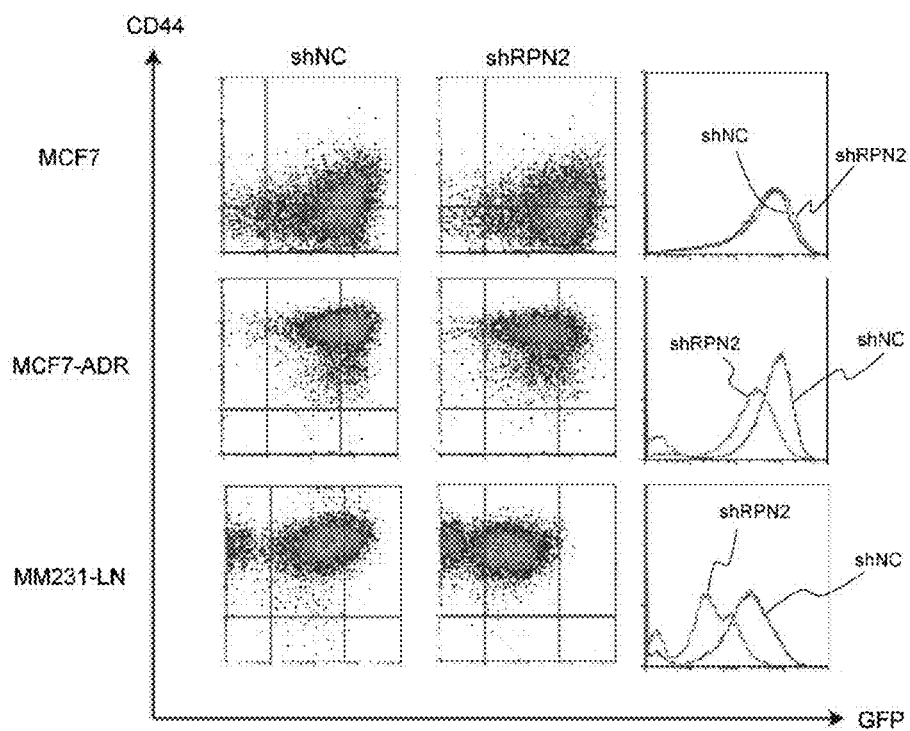

FIG. 3A
FIG. 3B
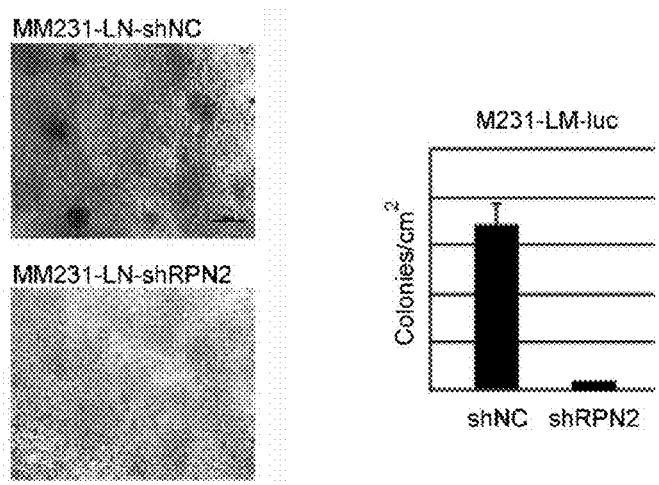
FIG. 4
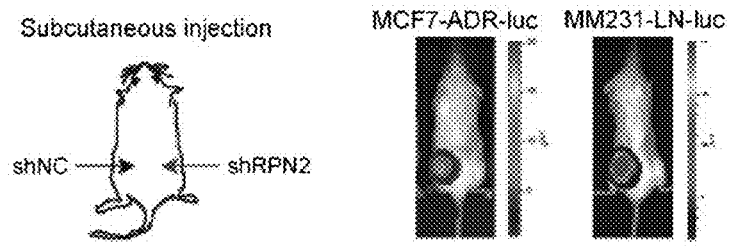
FIG. 5
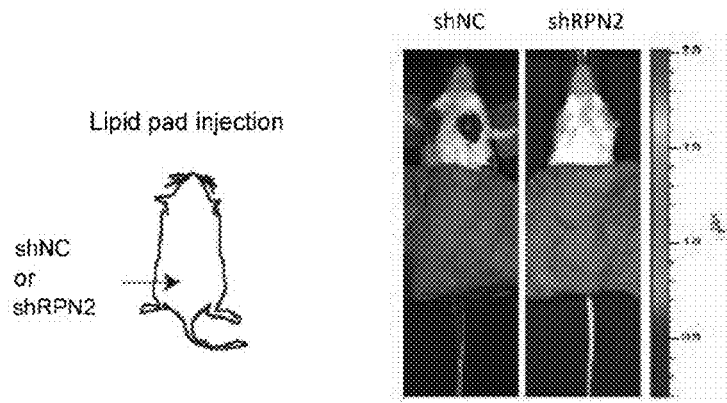

FIG. 6
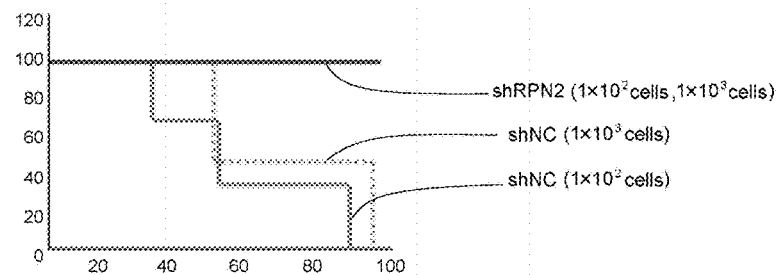
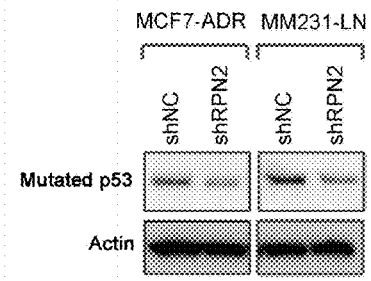
FIG. 7A
FIG. 7B
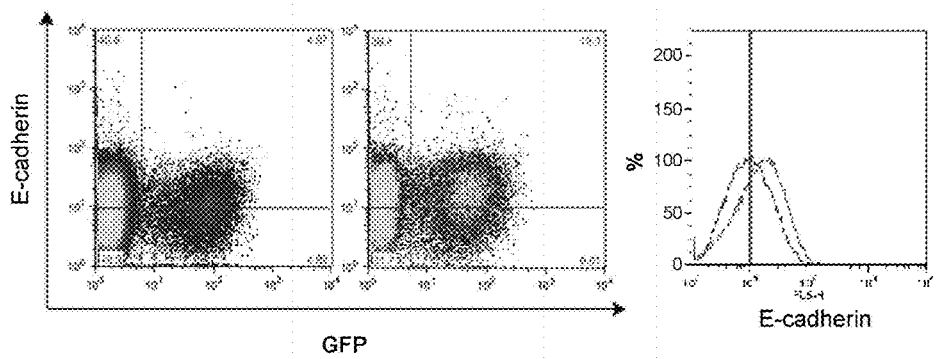

N: Nuclear fraction
C: Cytosol fraction

T phase : T1b
Lymph node metastasis : 22/26
100 μm

T phase : T3
Lymph node metastasis : 25/25 siRNA-carrier complex

Carrier ($A_6K$) alone

SEQUENCE LISTING

<160> NUMBER OF SEQ ID NOS: 26

<210> SEQ ID NO 1
<211> LENGTH: 2509
<212> TYPE: DNA
<213> ORGANISM: Homo sapiens

<400> SEQUENCE: 1

```
ttccagcgtt gcgagacggt cggttccaag tgggcctggg cgcggggag aggcgggtct      60 gtcctcggga actgcaaggc cctgtgagcg ggaggactgg gatcccggcc gcggctgctg     120
gaagcgtcga agctcagcgg gccgcggaca tgacctgtgt ttagaactca tcctggcccg     180
cagagcctgc cgcgagtccc tggcgtcccc tgtggcgggc tcttggagcc actttcccga    240
gcggaagtca gcccgcggct cggactccgg cgggacctgc tcggaggaat ggcgccgccg    300
ggttcaagca ctgtcttcct gttggccctg acaatcatag ccagcacctg ggctctgacg    360
cccactcact acctcaccaa gcatgacgtg gagagactaa aagcctcgct ggatcgccct    420
ttcacaaatt tggaatctgc cttctactcc atcgtgggac tcagcagcct tggtgctcag    480
gtgccagatg caaagaaagc atgtacctac atcagatcta accttgatcc cagcaatgtg    540
gattccctct tctacgctgc ccaggccagc caggccctct caggatgtga gatctctatt    600
tcaaatgaga ccaaagatct gcttctggca gctgtcagtg aggactcatc tgttacccag    660
atctaccatg cagttgcagc tctaagtggc tttggccttc ccttggcatc ccaagaagca    720
ctcagtgccc ttactgctcg tctcagcaag gaggagactg tgctggcaac agtccaggct    780
ctgcagacag catcccacct gtcccagcag gctgacctga ggagcatcgt ggaggagatt    840
gaggaccttg ttgctcgcct ggatgaactc ggggcgtgt atctccagtt tgaagaagga    900
ctggaaacaa cagcgttatt tgtggctgcc acctacaagc tcatggatca tgtggggact    960
gagccatcca ttaaggagga tcaggtcatc cagctgatga cgcgatctt cagcaagaag   1020 aactttgagt ccctctccga agccttcagc gtggcctctg cagctgctgt gctctcgcat   1080
aatcgctacc acgtgccagt tgtggttgtg cctgagggct ctgcttccga cactcatgaa   1140
caggctatct tgcggttgca agtcaccaat gttctgtctc agcctctgac tcaggccact   1200
gttaaactag aacatgctaa atctgttgct tccagagcca ctgtcctcca gaagacatcc   1260 ttcaccccctg taggggatgt ttttgaacta aatttcatga acgtcaaatt ttccagtggt   1320
tattatgact tccttgtcga agttgaaggt gacaaccggt atattgcaaa taccgtagag   1380
```

```
ctcagagtca agatctccac tgaagttggc atcacaaatg ttgatctttc caccgtggat    1440
aaggatcaga gcattgcacc caaaactacc cgggtgacat acccagccaa agccaagggc    1500
acattcatcg cagacagcca ccagaacttc gccttgttct tccagctggt agatgtgaac    1560
actggtgctg aactcactcc tcaccagaca tttgtccgac tccataacca gaagactggc    1620
caggaagtgg tgtttgttgc cgagccagac aacaagaacg tgtacaagtt tgaactggat    1680
acctctgaaa gaaagattga atttgactct gcctctggca cctacactct ctacttaatc    1740
attggagatg ccactttgaa gaacccaatc ctctggaatg tggctgatgt ggtcatcaag    1800
ttccctgagg aagaagctcc ctcgactgtc ttgtcccaga accttttcac tccaaaacag    1860
gaaattcagc acctgttccg cgagcctgag aagaggcccc ccaccgtggt gtccaataca    1920
ttcactgccc tgatcctctc gccgttgctt ctgctcttcg ctctgtggat ccggattggt    1980
gccaatgtct ccaacttcac ttttgctcct agcacgatta tatttcacct gggacatgct    2040
gctatgctgg gactcatgta tgtctactgg actcagctca acatgttcca gaccttgaag    2100
tacctggcca tcctgggcag tgtgacgttt ctggctggca tcggatgct ggcccagcag    2160 gcagtcaaga gaacagcaca ttagttccag aagaaagatg gaaattctga aaactgaatg    2220
tcaagaaaag gagtcaagaa caattcacag tatgagaaga aaatggaaa aaaaaaactt    2280 tatttaaaaa agaaaaaagt ccagattgta gttatacttt tgcttgtttt tcagtttccc    2340
caacacacag cagatacctg gtgagctcag atagtctctt tctctgacac tgtgtaagaa    2400
gctgtgaata ttcctaactt acccagatgt tgcttttgaa aagttgaaat gtgtaattgt    2460
tttggaataa agagggtaac aataggaaca aaaaaaaaa aaaaaaaaa    2509

<210> SEQ ID NO 2
<211> LENGTH: 21
<212> TYPE: RNA
<213> ORGANISM: Artificial Sequence
<220> FEATURE:
<223> OTHER INFORMATION: Sense strand for sequence A

<400> SEQUENCE: 2
ggccacuguu aaacuagaac a                                              21

<210> SEQ ID NO 3
<211> LENGTH: 21
<212> TYPE: RNA
<213> ORGANISM: Artificial Sequence
<220> FEATURE:
<223> OTHER INFORMATION: Antisense strand for sequence A

<400> SEQUENCE: 3
uucuaguuua acaguggccu g                                              21

<210> SEQ ID NO 4
<211> LENGTH: 21
<212> TYPE: DNA
<213> ORGANISM: Artificial Sequence
<220> FEATURE:
<223> OTHER INFORMATION: Sense strand for sequence B
<220> FEATURE:
<221> NAME/KEY: misc_feature
<222> LOCATION: (20)..(21)
<223> OTHER INFORMATION: n stands for deoxythymidine (dT)

<400> SEQUENCE: 4
cguguacaag uuugaacugn n                                              21
```

```
<210> SEQ ID NO 5
<211> LENGTH: 21
<212> TYPE: DNA
<213> ORGANISM: Artificial Sequence
<220> FEATURE:
<223> OTHER INFORMATION: Antisense strand for sequence B
<220> FEATURE:
<221> NAME/KEY: misc_feature
<222> LOCATION: (20)..(21)
<223> OTHER INFORMATION: n stands for deoxythymidine (dT)

<400> SEQUENCE: 5
caguucaaac uuguacacgn n                                              21

<210> SEQ ID NO 6
<211> LENGTH: 21
<212> TYPE: DNA
<213> ORGANISM: Artificial Sequence
<220> FEATURE:
<223> OTHER INFORMATION: Sense strand for sequence C
<220> FEATURE:
<221> NAME/KEY: misc_feature
<222> LOCATION: (20)..(21)
<223> OTHER INFORMATION: n stands for deoxythymidine (dT)

<400> SEQUENCE: 6
gccauccauu aaggaggaun n                                              21

<210> SEQ ID NO 7
<211> LENGTH: 21
<212> TYPE: DNA
<213> ORGANISM: Artificial Sequence
<220> FEATURE:
<223> OTHER INFORMATION: Antisense strand for sequence C
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxycytidine (dC)

<400> SEQUENCE: 7
auccuccuua auggauggcn n                                              21

<210> SEQ ID NO 8
<211> LENGTH: 21
<212> TYPE: DNA
<213> ORGANISM: Artificial Sequence
<220> FEATURE:
<223> OTHER INFORMATION: Sense strand for sequence D
<220> FEATURE:
<221> NAME/KEY: misc_feature
<222> LOCATION: (20)..(21)
<223> OTHER INFORMATION: n stands for deoxythymidine (dT)

<400> SEQUENCE: 8
gcaaugugga uucccucuun n                                              21

<210> SEQ ID NO 9
<211> LENGTH: 21
<212> TYPE: DNA
<213> ORGANISM: Artificial Sequence
<220> FEATURE:
<223> OTHER INFORMATION: Antisense strand for sequence D
<220> FEATURE:
<221> NAME/KEY: misc_feature
<222> LOCATION: (20)..(20)
<223> OTHER INFORMATION: n stands for deoxythymidine (dT)
```

```
<220> FEATURE:
<221> NAME/KEY: misc_feature
<222> LOCATION: (21)..(21)
<223> OTHER INFORMATION: n stands for deoxyguanosine (dG)

<400> SEQUENCE: 9
aagagggaau ccacauugcn n                                              21

<210> SEQ ID NO 10
<211> LENGTH: 21
<212> TYPE: DNA
<213> ORGANISM: Artificial Sequence
<220> FEATURE:
<223> OTHER INFORMATION: Sense strand for sequence E
<220> FEATURE:
<221> NAME/KEY: misc_feature
<222> LOCATION: (20)..(21)
<223> OTHER INFORMATION: n stands for deoxythymidine (dT)

<400> SEQUENCE: 10
ggugccagau gcaaagaaan n                                              21

<210> SEQ ID NO 11
<211> LENGTH: 21
<212> TYPE: DNA
<213> ORGANISM: Artificial Sequence
<220> FEATURE:
<223> OTHER INFORMATION: Antisense strand for sequence E
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxyguanosine (dG)

<400> SEQUENCE: 11
uuucuuugca ucuggcaccn n                                              21

<210> SEQ ID NO 12
<211> LENGTH: 21
<212> TYPE: DNA
<213> ORGANISM: Artificial Sequence
<220> FEATURE:
<223> OTHER INFORMATION: Sense strand for sequence F
<220> FEATURE:
<221> NAME/KEY: misc_feature
<222> LOCATION: (20)..(21)
<223> OTHER INFORMATION: n stands for deoxythymidine (dT)

<400> SEQUENCE: 12
ggaugugaga ucucuauuun n                                              21

<210> SEQ ID NO 13
<211> LENGTH: 21
<212> TYPE: DNA
<213> ORGANISM: Artificial Sequence
<220> FEATURE:
<223> OTHER INFORMATION: Antisense strand for sequence F
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxyguanosine (dG)

<400> SEQUENCE: 13
```

-continued aaauagagau cucacauccn n                                        21

<210> SEQ ID NO 14
<211> LENGTH: 21
<212> TYPE: DNA
<213> ORGANISM: Artificial Sequence
<220> FEATURE:
<223> OTHER INFORMATION: Sense strand for sequence G
<220> FEATURE:
<221> NAME/KEY: misc_feature
<222> LOCATION: (20)..(21)
<223> OTHER INFORMATION: n stands for deoxythymidine (dT)

<400> SEQUENCE: 14
ggugccagau gcaaagaaan n                                        21

<210> SEQ ID NO 15
<211> LENGTH: 21
<212> TYPE: DNA
<213> ORGANISM: Artificial Sequence
<220> FEATURE:
<223> OTHER INFORMATION: Antisense strand for sequence G
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxyguanosine (dG)

<400> SEQUENCE: 15
uuucuuugca ucuggcaccn n                                        21

<210> SEQ ID NO 16
<211> LENGTH: 21
<212> TYPE: DNA
<213> ORGANISM: Artificial Sequence
<220> FEATURE:
<223> OTHER INFORMATION: Sense strand for sequence H
<220> FEATURE:
<221> NAME/KEY: misc_feature
<222> LOCATION: (20)..(21)
<223> OTHER INFORMATION: n stands for deoxythymidine (dT)

<400> SEQUENCE: 16
ggccacuguu aaacuagaan n                                        21

<210> SEQ ID NO 17
<211> LENGTH: 21
<212> TYPE: DNA
<213> ORGANISM: Artificial Sequence
<220> FEATURE:
<223> OTHER INFORMATION: Antisense strand for sequence H
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxyguanosine (dG)

<400> SEQUENCE: 17
uucuaguuua acaguggccn n                                        21

<210> SEQ ID NO 18
<211> LENGTH: 21
<212> TYPE: DNA
<213> ORGANISM: Artificial Sequence

```
<220> FEATURE:
<223> OTHER INFORMATION: Sense strand for sequence I
<220> FEATURE:
<221> NAME/KEY: misc_feature
<222> LOCATION: (20)..(21)
<223> OTHER INFORMATION: n stands for deoxythymidine (dT)

<400> SEQUENCE: 18 ggguagacaua cccagccaan n                                                 21

<210> SEQ ID NO 19
<211> LENGTH: 21
<212> TYPE: DNA
<213> ORGANISM: Artificial Sequence
<220> FEATURE:
<223> OTHER INFORMATION: Antisense strand for sequence I
<220> FEATURE:
<221> NAME/KEY: misc_feature
<222> LOCATION: (20)..(21)
<223> OTHER INFORMATION: n stands for deoxyguanosine (dG)

<400> SEQUENCE: 19
uuggcugggu augucacccn n                                                  21

<210> SEQ ID NO 20
<211> LENGTH: 21
<212> TYPE: DNA
<213> ORGANISM: Artificial Sequence
<220> FEATURE:
<223> OTHER INFORMATION: Sense strand for sequence J
<220> FEATURE:
<221> NAME/KEY: misc_feature
<222> LOCATION: (20)..(21)
<223> OTHER INFORMATION: n stands for deoxythymidine (dT)

<400> SEQUENCE: 20
ggguaacaau aggaacaaan n                                                  21

<210> SEQ ID NO 21
<211> LENGTH: 21
<212> TYPE: DNA
<213> ORGANISM: Artificial Sequence
<220> FEATURE:
<223> OTHER INFORMATION: Antisense strand for sequence J
<220> FEATURE:
<221> NAME/KEY: misc_feature
<222> LOCATION: (20)..(20)
<223> OTHER INFORMATION: n stands for deoxythymidine (dT)
<220> FEATURE:
<221> NAME/KEY: misc_feature
<222> LOCATION: (21)..(21)
<223> OTHER INFORMATION: n stands for deoxycytidine (dC)

<400> SEQUENCE: 21
uuuguuccua uguuacccn n                                                   21

<210> SEQ ID NO 22
<211> LENGTH: 25
<212> TYPE: RNA
<213> ORGANISM: Artificial Sequence
<220> FEATURE:
<223> OTHER INFORMATION: Sense strand for sequence K

<400> SEQUENCE: 22
aagauagccu guucaugagu gucgg                                              25

<210> SEQ ID NO 23
<211> LENGTH: 25
<212> TYPE: RNA
```

```
<213> ORGANISM: Artificial Sequence
<220> FEATURE:
<223> OTHER INFORMATION: Antisense strand for sequence K

<400> SEQUENCE: 23
ccgacacuca ugaacaggcu aucuu                                           25

<210> SEQ ID NO 24
<211> LENGTH: 25
<212> TYPE: RNA
<213> ORGANISM: Artificial Sequence
<220> FEATURE:
<223> OTHER INFORMATION: Sense strand for sequence L

<400> SEQUENCE: 24
uuauggaguc ggacaaaugu cuggu                                           25

<210> SEQ ID NO 25
<211> LENGTH: 25
<212> TYPE: RNA
<213> ORGANISM: Artificial Sequence
<220> FEATURE:
<223> OTHER INFORMATION: Antisense strand for sequence L

<400> SEQUENCE: 25
accagacauu uguccgacuc cauaa                                           25

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Ala Ala Ala Ala Ala Ala Lys
1               5
```

METHOD AND COMPOSITION FOR THE TREATMENT, PREVENTION, AND DIAGNOSIS OF CANCER CONTAINING OR DERIVED FROM CANCER STEM CELLS

CROSS-REFERENCE TO RELATED APPLICATIONS

The present application is a division of U.S. application Ser. No. 13/817,763, filed on Feb. 19, 2013, entitled "METHOD AND COMPOSITION FOR THE TREATMENT, PREVENTION, AND DIAGNOSIS OF CANCER CONTAINING OR DERIVED FROM CANCER STEM CELLS," which claims priority under 35 U.S.C. § 365 to PCT/JP2011/064527 filed on Jun. 24, 2011, and under 35 U.S.C. § 119 to Japanese Application no. 2010-184764, filed on Aug. 20, 2010, the disclosures of which are incorporated herein by reference in their entireties.

REFERENCE TO THE SEQUENCE LISTING SUBMITTED VIA EFS-WEB

This application includes an electronically submitted sequence listing in .txt format that is submitted via EFS-Web. The .txt file contains a sequence listing entitled "2013-05-10_0283-0355PUS1_St25.txt" created on May 10, 2013 and is 10,916 bytes in size. The sequence listing contained in the .txt file is part of the specification and is hereby incorporated by reference herein in its entirety.

TECHNICAL FIELD

The invention relates to a method and composition for the treatment, prevention, and diagnosis of cancer containing or derived from cancer stem cells through targeting the RPN2 gene.

BACKGROUND ART

Accumulated evidence suggests that tumors are not uniform, but are often composed of heterogeneous cell types, subsets of which are responsible for the suppression, drug resistance, and metastasis of tumor. Such cells are referred to as cancer stem cells (or tumor-initiating cells). When cancer stem cells are targeted, it is expected to be able to treat and prevent the development, metastasis, and recurrence of cancer. However, markers defining cancer stem cells are unknown because the molecular basis of cancer stem cell phenotype remains largely unclear. In addition, no method has been established for treatment or prevention through targeting cancer stem cells.

The inventors previously demonstrated that ribophorin II (RPN2), a component of oligosaccharide transferase (OST) complex, controlled the drug resistance of breast cancer cells and that RPN2 silencing was a promising approach to overcoming the drug resistance of tumor (Patent literature 1). However, the mechanisms, such as the inhibition of cancer cell proliferation by suppressing RPN2 expression, remain unclear.

PRIOR ART LITERATURE

Patent Literature

Patent literature 1: International Patent Publication No. 2007/144985

DISCLOSURE OF INVENTION

Problems to be Resolved by the Invention

The objective of the invention is to provide a method and composition for the treatment, prevention, and diagnosis of cancer containing or derived from cancer stem cells.

Means for Solving the Problems

In the present application, the inventors demonstrate that RPN2 was highly expressed in the cancer stem cell fraction of breast cancer cells and that RPN2 knockdown inhibited the ability of colonization and invasion of cancer stem cells in vitro. Further analysis demonstrated that RPN2 knockdown reduced tumor formation and suppressed the ability of metastasis in vivo. Global proteomics analysis demonstrated that RPN2 knockdown altered the expression of 14-3-3ζ, which is known to regulate the TGF-β/Smad pathway. Thus, the inventors provide genetic and biological evidence that RPN2 can be important in maintaining the phenotype of cancer stem cells and that RPN2 can be a promising target for cancer stem cell therapy.

The present invention relates to
[1] a pharmaceutical composition comprising an RPN2 inhibitor for the treatment or prevention of cancer containing or derived from cancer stem cells;
[2] a pharmaceutical composition according to [1], wherein the cancer stem cells carry a mutated p53 gene;
[3] a pharmaceutical composition according to [1] or [2], wherein the RPN2 inhibitor is an siRNA against the RPN2 gene;
[4] a method for detecting cancer stem cells, comprising determining the presence or level of RPN2 expression; and
[5] a method according to [4] further comprising detecting a mutated p53 gene.

Effects of the Invention

The invention provides a method and composition for the treatment, prevention, and diagnosis of cancer containing or derived from cancer stem cells through targeting the RPN2 gene.

BRIEF DESCRIPTION OF THE DRAWINGS

FIG. 1 (A) provides unequal division of $CD44^+CD24^-$ cancer stem cells.

FIG. 1 (B) provides RPN2 expression analysis by RT-PCR.

FIG. 2 provides effects of RPN2 knockdown on the number of $CD44^+CD24^-$ cancer stem cells.

FIG. 3 (A) provides effects of RPN2 knockdown on colony forming activity.

FIG. 3 (B) provides Effects of RPN2 knockdown on the number of colonies formed.

FIG. 4 provides effects of RPN2 knockdown on tumorigenicity.

FIG. 5 provides effects of RPN2 knockdown on tumor metastasis.

FIG. 6 provides effects of RPN2 knockdown on lethality.

FIG. 7 (A) provides Effects of RPN2 knockdown on mutated p53 expression.

FIG. 7 (B) provides effects of RPN2 knockdown on E-cadherin expression.

BEST MODE FOR CARRYING OUT THE INVENTION

Figure 8:
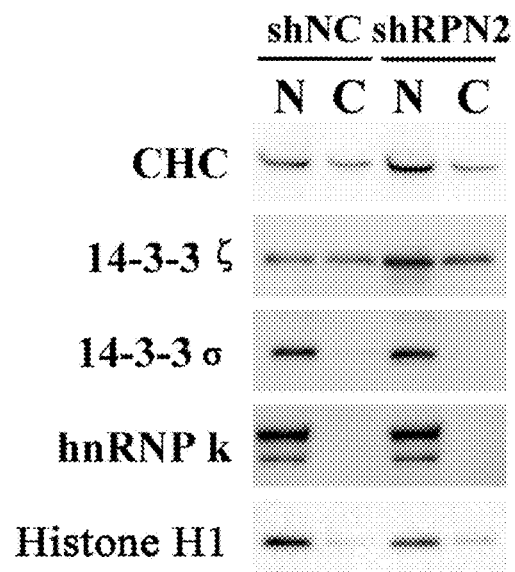
FIG. 8 provides effects of RPN2 knockdown on 14-3-3ζ expression.

The invention provides a pharmaceutical composition containing an RPN2 inhibitor for the treatment or prevention of cancer containing or derived from cancer stem cells. In addition, the invention provides a method for the treatment or prevention of cancer containing or derived from cancer stem cells, comprising administering the pharmaceutical composition of the invention to a subject.

The term "cancer stem cells," as used herein, refers to cancer cells having pluripotency and self-renewal ability (also referred to herein as self-renewal and differentiation ability). Cancer cells include any cancer cells, such as breast, stomach, colorectal, lung, prostate, and hematopoietic cancer cells. Besides self-renewal and differentiation ability, cancer stem cells may be resistant to anticancer agents (drug resistance) and have an ability to invade surrounding tissues and/or metastasize to distant sites in the body (invasion and metastasis ability). It is considered that the development, metastasis, and recurrence of cancer could be treated and prevented by targeting cancer stem cells. The invention is useful for such treatment and prevention of cancer through targeting cancer stem cells.

In one embodiment, the cancer stem cells have an increased expression level of ribophorin II (RPN2). "RPN2" is one of the components (subunit) of the oligosaccharide transferase (OST) complex, which exists in the rough endoplasmic reticulum and functions to add an N-linked sugar chain to a nascent polypeptide chain. Human RPN2 is a basic membrane protein consisting of 631 amino acids. The sources of the RPN2 include, but are not limited to, for example, animals, preferably mammals, more preferably primates, and even more preferably humans. "RPN2 gene" is a gene that encodes RPN2. The base sequence of the human RPN2 gene is shown in SEQ ID NO: 1.

The inventors found that the knockdown of RPN2 expression with a short hairpin RNA (shRNA) in the cancer stem cell fraction of CD44$^+$/CD24$^-$ of breast cancer inhibited the ability of the colony formation and invasion of the cancer stem cells in vitro and abrogated tumorigenicity and invasion and metastasis ability in an immunodeficient animal (i.e., in vivo). As described above, cancer stem cells can have self-renewal and differentiation ability, drug resistance, and invasion and metastasis ability. Thus, RPN2 involved in all of these will serve as a marker of cancer stem cells. Further, targeting RPN2 may allow the treatment and prevention of cancers containing or derived from cancer stem cells.

In another embodiment, cancer stem cells carry a mutated p53 gene. "P53" is a tumor suppressor gene product. Mutations in the p53 gene have been found in many human cancers (Adorno, M. et al., Cell, 137: 87-98 (2009); Wang, S. P. et al., Nat. Cell Biol., 11: 694-704 (2009); Muller, P. A. et al., Cell, 139: 1327-1341 (2009); Morton, J. P. et al., Proc. Natl. Acad. Sci. USA, 107:246-251 (2010)). Mutations in the p53 gene preferably include, but are not limited to, substituted point mutations (missense mutations), which cause no frameshift mutation, or deletion mutations (codon deletion mutations).

The inventors found that the knockdown of RPN2 expression in cell lines with mutated p53 reduced the level of the mutated p53 protein and suppressed E-cadherin expression. In addition, the inventors found that 14-3-3ζ expression was decreased in cancer cells with high RPN2 expression and was increased by RPN2 knockdown. It is known that 14-3-3ζ acts to degrade mutated p53 through mdm2.

Cancer cells exhibit a phenomenon referred to as epithelial-mesenchymal transition (EMT). The expression of E-cadherin involved in cell adhesion is reduced upon EMT, resulting in the invasion or metastasis of cancer cells. The above results suggest that RPN2 reduces 14-3-3ζ expression to stabilize mutated p53 and cause EMT in cancer cells, resulting in the invasion or metastasis of cancer cells.

Mutated P53 is involved in the self-renewal and differentiation and invasion and metastasis abilities of cancer cells. Many studies have been conducted on p53. However, no report has been published on the successful treatment or prevention of cancer through targeting p53. RPN2 is involved in self-renewal and differentiation and invasion and metastasis abilities, besides drug resistance. Thus, inhibiting RPN2 not only eliminates the drug resistance of cancer cells, but also inhibits the self-renewal and differentiation and invasion and metastasis abilities of cancer cells through inhibiting the effects of mutated p53 upstream. Detecting the presence of mutated p53, as well as RPN2 expression, allows more accurate identification of cancer cells having mutated p53, for which inhibiting RPN2 is effective. In addition, inhibiting RPN2 allows more effective treatment and prevention of cancers associated with mutated p53 than targeting the mutated p53.

The term "RPN2 inhibitor," as used herein, refers to any substance that inhibits RPN2 gene expression or the effects of RPN2 gene product. RPN2 is little expressed in normal tissues, excluding the placenta. Thus, RPN2 inhibitors have no substantial effects on cells other than cancer cells in subjects, excluding pregnant women, and are useful as specific therapeutics for cancer without adverse effects. Subjects preferably include, but are not limited to, for example, animals, mammals, more preferably primates, and even more preferably humans For example, substances that inhibit RPN2 gene transcription, those that bind to or degrade RPN2 transcripts, and those that bind to the RPN2 protein can be used as RPN2 inhibitors. Examples of substances that bind to the RPN2 protein include an anti-RPN2 antibody or fragments thereof (Fab, F(ab')2, etc.), and other components that bind to RPN2 in the oligosaccharide transferase (OST) complex. Examples of substances that bind to or degrade RPN2 transcripts include antisense RNA, ribozymes, small interfering RNA (siRNA), and micro RNA (miRNA) against the RPN2 gene. siRNA, miRNA, and the like, which cause RNA interference (RNAi) against the RPN2 gene, are preferably used as RPN2 inhibitors. RNA interference refers to a phenomenon in which gene expression is suppressed by a double-stranded (ds) RNA molecule in a sequence-specific manner. For example, RNA interference results from target mRNA cleavage by siRNA, gene silencing through heterochromatin formation in a target DNA region by siRNA, and translational and transcriptional repression and mRNA degradation by miRNA. siRNA is preferably used in the present invention because its sequence can be designed based on the target RPN2 gene sequence and can be artificially synthesized.

Such siRNA can be obtained by any method known in the art. For example, siRNA can be chemically synthesized by the phosphoramidite method, which is also employed for the chemical synthesis of DNA, through the sequential condensation reaction of a single base at a time towards the 5' to 3' end. Preferably, the hydroxyl groups of the 2' ends of individual ribonucleotides are protected to prevent the degradation by RNase during synthesis. Such protecting groups include 2'-O-t-butyldimethylsilyl (2'-tBDMS), 2'-O-(triisopropylsilyloxy)methyl (2'-TOM), and 5'-silyl-2'-acetoxyethoxy (2'-ACE) groups.

siRNA against the RPN2 gene has a sequence corresponding to a predetermined sequence of the RPN2 gene, i.e., a sequence corresponding to a part of a target mRNA sequence. For example, dsRNA (sequence A) consisting of the RNAs of SEQ ID NOS: 2 (sense strand) and 3 (antisense strand), corresponding to the position 1,194-1,212 of the RPN2 gene sequence (SEQ ID NO: 1), can be used as siRNA. This dsRNA has 2-base overhangs at the 3' ends of each strand. Thus, the double-stranded region is 19 bases in length. SEQ ID NOS: 4-25 show the sequences of the sense and antisense strands of the siRNAs (sequences B-L) against the RPN2 gene, disclosed in Patent literature 1. These pairs (dsRNAs) can be used as RPN2 inhibitors in the present invention.

miRNA is a small RNA molecule that encodes no protein. Several hundred kinds of miRNA exist on the genome. miRNA is transcribed into nucleotides of several hundred to several thousand bases and eventually undergoes processing into nucleotide dimers of 19-24 bases to suppress the gene expression through the translational repression, degradation, and transcriptional regulation of mRNA having a nucleotide sequence complementary to the miRNA. RPN2 expression is also regulated by multiple miRNAs. Such miRNAs can be artificially synthesized to be used in the present invention as RPN2 inhibitors in order to suppress RPN2 gene expression. Known miRNA sequences that may inhibit RPN2 gene expression can be retrieved from public databases (e.g., TargetScan Release3.1).

The pharmaceutical composition of the present invention may be administered through either systemic or local administration. The route of administration may be any route, such as intravenous, subcutaneous, intraperitoneal, intramuscular, and intranasal routes. The pharmaceutical composition of the present invention may further contain any ingredients used in the field of drug formulation, such as excipients, diluents, and stabilizers. For example, if an RPN2 inhibitor is a protein like an antibody, the pharmaceutical composition may further contain ingredients commonly used in the field of protein formulation. For example, if an RPN2 inhibitor is a nucleic acid like siRNA, any substance (e.g., liposome) for introducing a nucleic acid may be contained. The transfection agent containing a peptide surfactant, described in WO 2010/024262, can be suitably used for the present invention, because it shows low toxicity, high efficiency for a target gene to reach an affected area, and high efficiency of target gene suppression and, therefore, can be systemically administered.

The amount of an RPN2 inhibitor, contained in the pharmaceutical composition of the present invention, varies with administration methods, tumor types and sizes, patient's conditions, and concomitant drugs, and can be appropriately determined by those skilled in the art. For example, when an siRNA is used as an RPN2 inhibitor, the amount is desirably 1-10 nmol/kg for local administration and 2-50 nmol/kg for systemic administration.

The present invention provides a method of detecting cancer stem cells, comprising determining the presence or level of RPN2 expression.

RPN2 exists in the cytoplasm. Thus, to detect RPN2, an extract containing RNA and proteins is prepared from cells or tissues obtained from a subject. In the extract, transcripts (RPN2 mRNA) and translation products (RPN2 protein) are detected. For the detection of RPN2 protein, any methods known in the art, such as Northern blotting and reverse transcriptase-polymerase chain reaction (RT-PCR), can be employed. For the detection of RPN2 protein, any methods known in the art, for example, immunological methods using an anti-RPN2 antibody (Western blotting and ELISA), can be employed. RPN2 is little expressed in normal tissues, excluding the placenta. Thus, the presence of RPN2 expression or high-level RPN2 expression indicates the involvement of RPN2 in cancer. For the treatment and prevention of such cancers, treatments with the pharmaceutical composition of the present invention, containing an RPN2 inhibitor, are effective.

In one embodiment, the detection method of the present invention further comprises detecting a mutated p53 gene. A mutated p53 gene can be detected by any detection and analysis methods of nucleic acid using hybridization, electrophoresis, nucleic acid amplification, and sequencing known in the art. As described above, when a mutated p53 exists in cancer cells expressing RPN2, cancers associated with the mutated p53 can be effectively treated and prevented by inhibiting the RPN2. Thus, the detection method of the present invention is useful as a diagnosis method for determining effective treatment and prevention methods.

Hereinafter, the present invention will be described in detail using examples. However, the invention is not limited to these examples.

EXAMPLES

Example 1

Human breast cancer cell line MCF7-ADR was divided into two cell fractions, CD44$^+$CD24$^-$ and CD44$^+$CD24$^+$, and were cultured for seven days. Only the CD44$^+$CD24$^-$ fraction had an unequal division, a property of cancer stem cells (FIG. 1A).

Ribophorin II (RPN2) expression was analyzed by RT-PCR. As a result, RPN2 expression in CD44$^+$CD24$^-$ (cancer stem cells) was increased about 20-fold as compared with that in CD44$^+$CD24$^+$ (non-cancer stem cells) (FIG. 1B).

Example 2

Human breast cancer cells with RPN2 expression constitutively knocked down was generated using the shRPN2 vector. Three human breast cancer cell lines, MCF7, MCF7-ADR, and MDA-MB-231LN (MM231-LN), were used. MCF7 is the parent cell line of MCF7-ADR (drug-resistant cell line), i.e., hormone receptor-positive and drug-sensitive non-malignant breast cancer cells. MM231-LN is a hormone receptor-negative, highly metastatic and highly malignant cell line.

The respective cells obtained were incubated in the presence of 10 nM docetaxel for 96 hours. Subsequently, CD44$^+$CD24$^-$ cancer stem cells were counted. As a result, the numbers of CD44$^+$CD24$^-$ cancer stem cells were significantly reduced for MCF7-ADR and MM231-LN cells introduced with the shRPN2 vector, as compared with those introduced with a control vector (shNC) (FIG. 2).

Example 3

One characteristic of cancer stem cells is a colony-forming ability in plane (dish) culture. As shown in FIG. 3A (upper) (MM231-LN-shNC), MM231-LN cells formed many colonies. The colony-forming ability was significantly suppressed where the shRPN2 vector was introduced (FIG. 3A, lower, MM231-LN-shRPN2). FIG. 3B shows the number of colonies formed.

Example 4

Another characteristic of cancer stem cells is that even a small number of cells can form an established tumor when transplanted into an animal. In the present study, we compared two human breast cancer cell lines, MCF7-ADR and MM231-LN, with (shRPN2) or without (shNC) RPN2 knockdown. The cells introduced with the shRPN2 vector were transplanted into the right side of the back of a mouse (6-week-old female NOD-Scid mouse), while those introduced with the shNC vector were transplanted into the left side. The numbers of cells transplanted were $1\times10^4$ cells/site for MCF7-ADR and $1\times10^2$ cells/site for MM231-LN.

As a result, both cell lines introduced with the shRPN2 vector lost tumorigenicity, as shown in the mouse imaging (FIG. 4, middle (MCF7-ADR-luc) and right (MM231-LN-luc)). The results are summarized in Table 1.

TABLE 1

| | | Tumorigenicity | |
|---|---|---|---|
| Cell line | Number of cells | shNC | shRPN2 |
| MCF7-ADR-luc | $1 \times 10^4$ cells/site | 4/4 | 1/4 |
| MM231-LN-luc | $1 \times 10^2$ cells/site | 5/5 | 0/5 |

Example 5

MM231-LN cell is a highly malignant and highly metastatic one. This cell metastasizes to the lymph nodes under the armpit and chest, resulting in 100% lethality, when transplanted into the mouse mammary gland. In this system, cells introduced with the shRPN2 vector were compared with those introduced with the shNC vector. As a result, lymph node metastasis was significantly suppressed for the group of shRPN2 vector (FIG. 5). The results are summarized in Table 2.

TABLE 2

| | | Tumorigenicity (metastasis) | |
|---|---|---|---|
| Cell line | Number of cells | shNC | shRPN2 |
| MM231-LN-luc | $1 \times 10^2$ cells/site | 5/5 (3/5) | 1/5 (0/5) |
| | $1 \times 10^3$ cells/site | 5/5 (5/5) | 1/5 (0/5) |

Example 6

As a result of the long-term observation of the mice according to Example 5, all the mice transplanted with $1\times10^2$ or $1\times10^3$ cells for the shNC group become lethal, while all the mice transplanted with $1\times10^2$ or $1\times10^3$ cells for the shRPN2 group survived (FIG. 6). In FIG. 6, the vertical and horizontal axes represent metastasis-free survival (%) and time (days), respectively.

Example 7

Two cell lines, MCF7-ADR and MM231-LN, with RPN2 knocked down by the introduction of the shRPN2 vector, were examined regarding the expression of mutated p53 protein by Western blotting. As a result, the mutated p53 expression was significantly reduced in both cell lines (FIG. 7A).

In addition, it is demonstrated that RPN2 knockdown with shRPN2 induced E-cadherin expression (FIG. 7B). FIG. 7B (left) indicates the results for shNC. FIG. 7B (middle) indicates the results for shRPN2. FIG. 7B (right) indicates E-cadherin-positive cell rates (%).

E-cadherin expression disappears when cancer cells exhibit epithelial-mesenchymal transition (EMT). It is said that cancer cells with reduced E-cadherin expression are more likely to metastasize. Knocking down RPN2 expression in cells with high RPN2 expression using shRPN2 increased the E-cadherin expression. This fact supports the fact that PRN2 induces EMT.

Example 8

To investigate the mechanism by which mutated p53 expression is regulated by RPN2, proteins whose expressions were altered by the introduction of the shRPN2 vector into a cell were analyzed using a proteome technique. As a result, the involvement of 14-3-3ζ was demonstrated (FIG. 8). 14-3-3ζ acts to degrade the mutated p53 through mdm2. In cells with enhanced RPN2, mutated p53 is stabilized, and E-cadherin is decreased, because 14-3-3ζ expression is reduced. Thus, it is possible that the cells might be destined to direct EMT involved in metastasis.

Example 9

Figure 9:
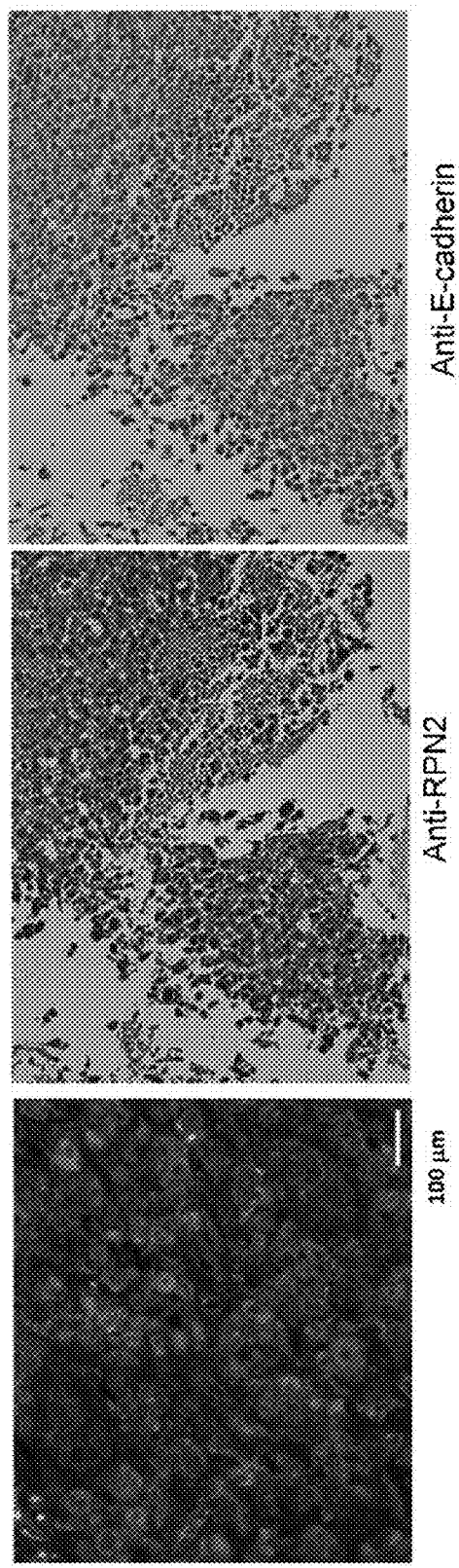
FIG. 9 provides immunohistochemical staining of tumors formed by transplanting MM231-LN cells into an animal.

MM231-LN cells were transplanted into an animal. The tumor formed was examined by immunohistochemical staining using three colors: DAPI for nuclear-specific staining (blue), anti-RPN2 antibody (green), and anti-mutated p53 antibody (red) (FIG. 9, left). The staining patterns of RPN2-positive and mutated p53-positive cells were consistent. In addition, RPN2 expression was examined by staining using the ABC method (FIG. 9, middle). In cancer cells with high RPN2 expression, strongly stained in FIG. 9 (middle), E-cadherin expression was reduced (FIG. 9, right).

Example 10

Figure 10:
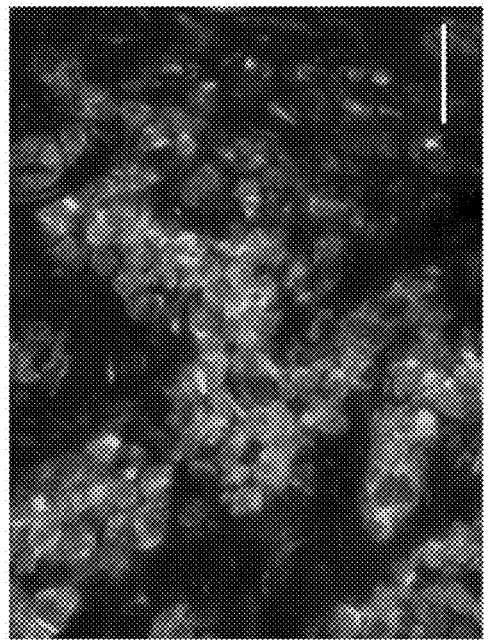
FIG. 10 provides RPN2 and mutated p53 expressions in breast cancer tissue of a human patient with breast cancer.
Figure 10:
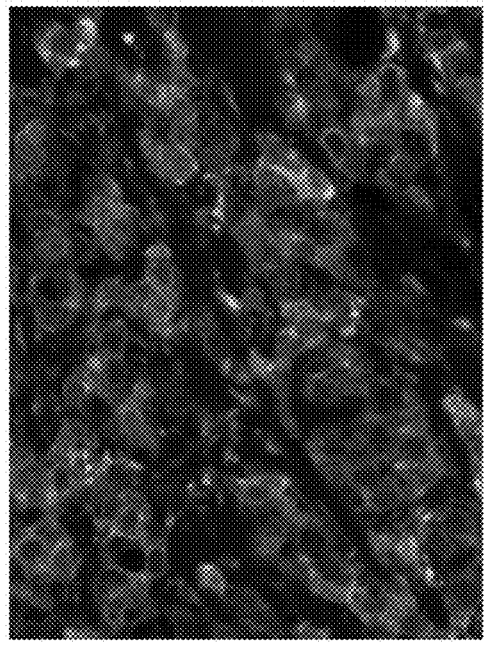

Breast cancer tissue specimens obtained from two human patients with breast cancer were examined by fluorescent immunostaining using three colors: DAPI for nuclear-specific staining (blue), anti-RPN2 antibody (green), and anti-mutated p53 antibody (red). The tissue specimens were obtained from primary tumors, and both of which were positive for lymph node metastasis. In both specimens, the staining patterns of RPN2- and mutated p53-positive cells were consistent. This supports the in vitro results in Example 9 (FIG. 10).

Example 11

Apoptosis of breast cancer cells and tumor shrinkage of breast cancer by the administration of siRNA against the RPN2 gene in a dog with spontaneous breast cancer PCR analysis of spontaneous cancer tissue (including mammary gland cancer) of a dog demonstrated that RPN2 tended to be highly expressed also in breast cancer tissue of a dog. siRNA against canine RPN2 was designed and mixed with the aqueous solution of nucleic acid transport carrier (a transport carrier containing a peptide surfactant ($A_6K$ (SEQ ID NO: 26): Patent Publication 2010-222338) was used as a nucleic acid transport carrier at a final concentration of 0.5%) to prepare an siRNA-carrier complex (final concentration: 1 mg/mL).

The above siRNA-carrier complex was locally administered to the tumor of spontaneous breast cancer of a dog (golden retriever weighing about 40 kg) twice every three days. The tumor was surgically resected on day 3 after the last administration. Saline or carrier ($A_6K$ (SEQ ID NO: 26)) alone was administered as a control.

Before the administration of the siRNA-carrier complex, gross tumor size was 36.3 mm in long diameter and 17.1 mm in short diameter. On day 3. after the last administration, the size was 24.9 mm in long diameter and 15.6 mm in short diameter (43% reduction in gross tumor volume (GTV)).

Figure 11:
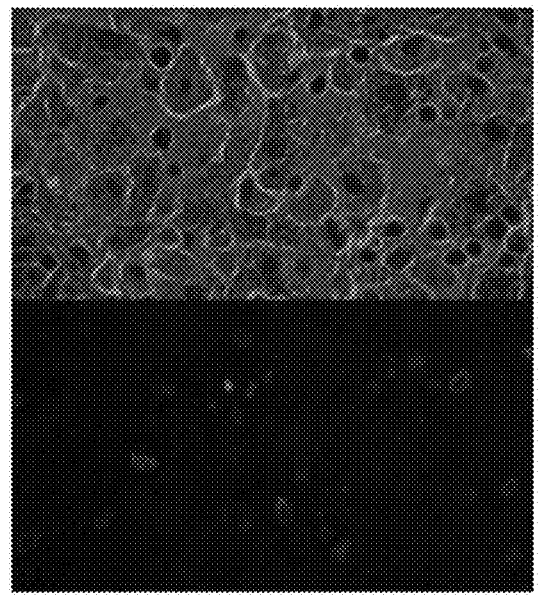
FIG. 11 provides tumor apoptosis examined by TUNEL assay. Tumor apoptosis of breast cancer was demonstrated to be strongly induced by the intratumoral delivery of RPN2-siRNA/A$_6$K (SEQ ID NO: 26) on day 3 after administration.
Figure 11:
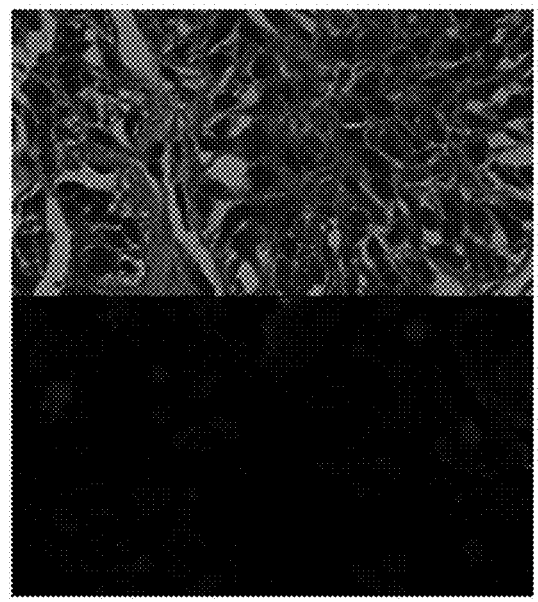
Figure 12:
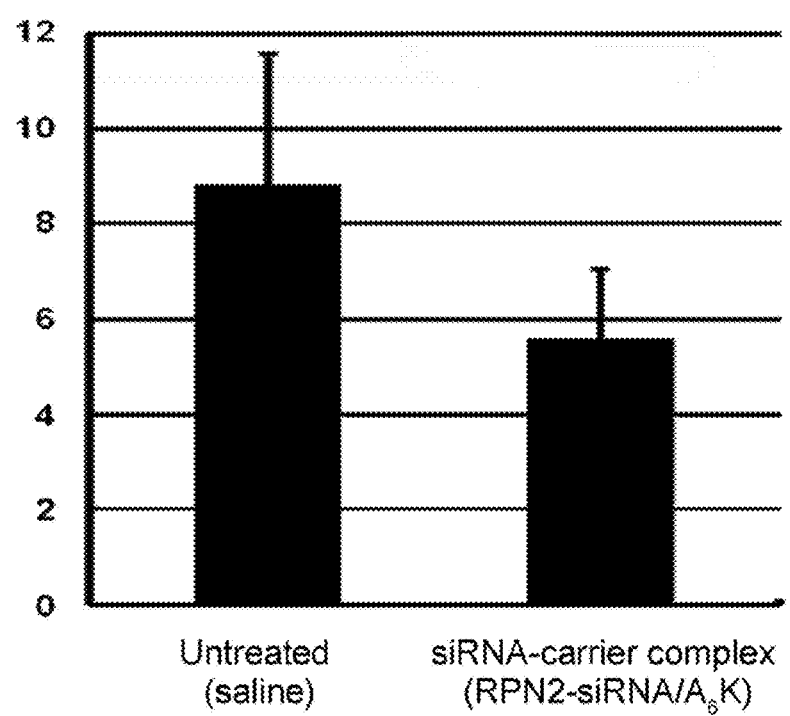
FIG. 12 provides RPN2 knockdown analysis in canine breast cancer. The RPN2-siRNA/A$_6$K (SEQ ID NO: 26) showed about 50% inhibition of RPN2 mRNA as compared with the control (saline) (n=3, p<0.001).

Thin section observation and TUNEL assay of surgically-resected tumor tissue demonstrated apoptotic tumor cells caused by the administration of the siRNA-carrier complex. No structure characteristic of the tumor tissue was observed after the administration (FIG. 11, right). The administration of $A_6K$ (SEQ ID NO: 26) alone caused no significant alteration in the tumor tissue (FIG. 11, left). The administration of the siRNA-carrier complex knocked down the RPN2 mRNA by about 50% (FIG. 12).

INDUSTRIAL APPLICABILITY

The invention provides a method and composition for the treatment, prevention, and diagnosis of cancer containing or derived from cancer stem cells through targeting the RPN2 gene.

The invention claimed is:

1. A method of treating a cancer containing or derived from cancer stem cells comprising a step of administering an siRNA-carrier complex comprising an siRNA against ribophorin II (RPN2) and a transport carrier to a subject in need thereof, wherein the cancer stem cells have a mutated p53 gene, and wherein the siRNA interferes with RPN2 gene expression in an in vitro assay.

2. The method of claim 1, wherein the transport carrier comprises the peptide AAAAAAK (SEQ ID NO: 26).

3. The method of claim 1, wherein the siRNA-carrier complex is administered locally.

4. The method of claim 1, wherein the siRNA-carrier complex is administered systemically.

5. The method of claim 1, wherein a double-stranded region of the siRNA is 19 bases in length.

6. The method of claim 1, wherein a double-stranded region of the siRNA comprises position of 1,194 of the RPN2 gene sequence (SEQ ID NO: 1).

7. The method of claim 1, wherein a double-stranded region of the siRNA corresponds to at least position 1,212 of the RPN2 gene sequence (SEQ ID NO: 1).

8. The method of claim 1, wherein the siRNA corresponds to positions comprises 1,194-1,212 of the RPN2 gene sequence (SEQ ID NO: 1).

9. The method of claim 1, wherein the siRNA comprises RNA comprises SEQ ID NO: 2.

10. The method of claim 1, wherein the siRNA comprises RNA comprising SEQ ID NO: 3.

11. The method of claim 1, further comprising administering a substance for introducing a nucleic acid.

12. The method of claim 11, wherein the substance for introducing a nucleic acid is liposome.

* * * * *